US012806333B2

(12) United States Patent
Dang et al.

(10) Patent No.: US 12,806,333 B2
(45) Date of Patent: Nov. 24, 2026

(54) SYSTEM AND METHOD FOR DELIVERING A FLUID FROM A CONTAINER TO AN INFUSION LINE

(71) Applicant: CareFusion 303, Inc., San Diego, CA (US)

(72) Inventors: Kenny Dang, Laguna Niguel, CA (US); Srinivas Ramakrishnarao Peddi, Pune (IN); Janice R. Pak, Centennial, CO (US)

(73) Assignee: CAREFUSION 303, INC., San Diego, CA (US)

( * ) Notice: Subject to any disclaimer, the term of this patent is extended or adjusted under 35 U.S.C. 154(b) by 749 days.

(21) Appl. No.: 18/328,695

(22) Filed: Jun. 2, 2023

(65) Prior Publication Data

US 2023/0390486 A1 Dec. 7, 2023

Related U.S. Application Data

(60) Provisional application No. 63/349,518, filed on Jun. 6, 2022.

(51) Int. Cl.
*A61M 5/142* (2006.01)
*A61M 5/168* (2006.01)

(52) U.S. Cl.
CPC ...... *A61M 5/1424* (2013.01); *A61M 5/16813* (2013.01); *A61M 5/16859* (2013.01); *A61M 5/16886* (2013.01)

(58) Field of Classification Search
CPC ............ A61M 5/1424; A61M 5/16813; A61M 5/16859; A61M 5/16886; A61M 5/16854; A61M 5/1483; A61M 5/148; A61M 5/1486; A61H 9/005; A61H 9/0078
See application file for complete search history.

(56) References Cited

U.S. PATENT DOCUMENTS 5,368,569 A 11/1994 Sanese
5,824,000 A * 10/1998 Pavlo ................. A61M 5/1483 604/153
7,905,858 B2 3/2011 Temple
(Continued)

FOREIGN PATENT DOCUMENTS

CN 109550108 A * 4/2019 ........ A61M 5/16804

OTHER PUBLICATIONS

International Search Report and Written Opinion for Application No. PCT/US2023/023017, dated Aug. 16, 2023, 14 pages.

*Primary Examiner* — Chelsea E Stinson
*Assistant Examiner* — Mark Golovan
(74) *Attorney, Agent, or Firm* — MASCHOFF BRENNAN

(57) ABSTRACT

A fluid container is encompassed by a custom fluid container pressure sleeve, which is configured to wrap around, connect and form to the malleable fluid container such that, when the fluid container pressure sleeve is inflated with a gas, the fluid container pressure sleeve applies an inward directional pressure to the malleable fluid container from an exterior of the malleable fluid container to compress the malleable fluid container. A pump connected to the fluid container pressure sleeve is activated to provide the gas to the fluid container pressure sleeve to compress the malleable fluid container and direct a fluid (e.g., the blood product) within the malleable fluid container toward and through a connected infusion tubing.

19 Claims, 4 Drawing Sheets

(56) References Cited

U.S. PATENT DOCUMENTS

| | | | | |
|---|---|---|---|---|
| 2003/0208158 | A1* | 11/2003 | Lampropoulos .... | A61M 5/1483<br>604/142 |
| 2007/0185451 | A1 | 8/2007 | Sato | |

* cited by examiner

SYSTEM AND METHOD FOR DELIVERING A FLUID FROM A CONTAINER TO AN INFUSION LINE

CROSS-REFERENCE TO RELATED APPLICATION

This application claims the benefit of U.S. Provisional Application No. 63/349,518, filed on Jun. 6, 2022, the entirety of each of which is incorporated herein by reference for all purposes.

BACKGROUND

This application relates generally to automated blood transfusions.

Delivering large amounts of blood over a small period of time, such as in trauma situations, may include use of an in-line hand pump, or in some cases pressure sleeves around the blood IV bag that are also manually pumped operated. This is ergonomically not ideal and results in fatigue for the clinician. It may not always be the most efficient method for trying to increase the flow of blood to the patient as in many cases the hand pump causes back flow of blood as the hand pump refills with blood with each pump cycle.

SUMMARY

This subject technology provides an IV set designed for large volume delivery of fluids at high flow rates, particularly addressing the delivery of large volumes of blood in trauma situations. The IV set is designed to be used with a malleable fluid container, particularly a blood product, and includes a custom fluid container pressure sleeve and a mechanical or electric pump.

During the delivery phase, the malleable fluid container is encompassed by a fluid container pressure sleeve, which is configured to wrap around, connect and form to the malleable fluid container such that, when the fluid container pressure sleeve is inflated with a gas, the fluid container pressure sleeve applies an inward directional pressure to the malleable fluid container from an exterior of the malleable fluid container to compress the malleable fluid container. A pump connected to the fluid container pressure sleeve is activated to provide the gas to the fluid container pressure sleeve to compress the malleable fluid container and direct a fluid (e.g., the blood product) within the malleable fluid container toward and through a connected infusion tubing.

According to various aspects of the subject technology, an infusion system for intravenous delivery of a fluid from a fluid container, comprises a malleable fluid container configured to store a fluid and deliver the fluid via a connected infusion tubing; a fluid container pressure sleeve configured to wrap around, connect and form to the malleable fluid container such that, when the fluid container pressure sleeve is inflated with a gas, the fluid container pressure sleeve applies an inward directional pressure to the malleable fluid container from an exterior of the malleable fluid container; a pump configured to provide the gas to the fluid container pressure sleeve; and a pressure measuring device configured to measure a pressure associated with the malleable fluid container by the fluid container pressure sleeve.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Figure 1:
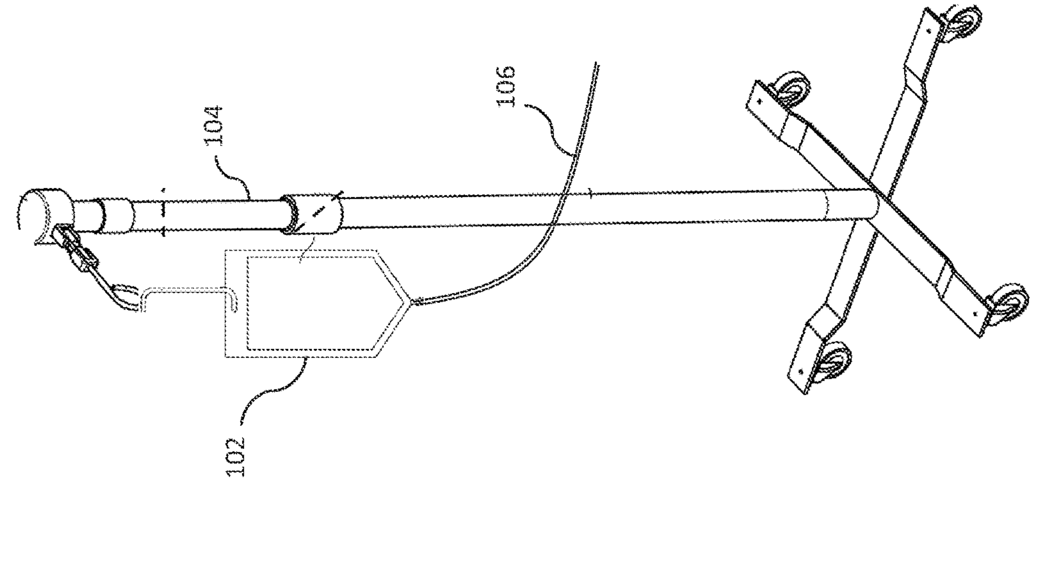
FIG. 1 depicts an example fluid delivery system.

FIG. 1 depicts a fluid delivery system according to various implementations of the subject technology. Intravenous fluids, such as a blood infusate, are contained in malleable (e.g. flexible) bags, commonly referred to as intravenous or "IV" bags. These bags are equipped with multiple septums or other fluid connections that which permit connection of the bag to a tube that feeds the fluid to the patient. The bags are floppy and subject to puncture if they come into contact with sharp items. Alternate containers, which may be more prevalent in other countries, include glass bottles and soft plastic bottles.

Administration of these IV fluids, regardless of the container, requires that the fluid container be suspended at some height, typically 0.5-1.0 meter, above the patient or an infusion pump. This container is then connected by a flexible tube to either the patient directly or to the infusion pump. Mounting the fluid container above the delivery point generates a positive pressure due to gravity at the connection of the infusion tube to the patient or pump. One embodiment of such a mounting is illustrated in FIG. 1, wherein an IV bag 102 is mounted in an elevated position on a pole 104. A fluid delivery line 106 leads from the bag 102. The administration may include a drip chamber (not shown). Relatively inexpensive tubing may be used such as polyvinyl chloride ("PVC") tubing or similar type tubing.

A separate infusion pump may be used to infuse the fluid within the fluid container into the patient. Some infusion pumps act as flow control devices to act on the respective tube or fluid conduit of the fluid administration set to move the fluid from the fluid container through the conduit to the patient. Some pumps may be programmed with operating parameters to infuse the fluid from the respective fluid container into the patient at the particular rate prescribed for that fluid by a physician. Fluids which may be infused by the subject technology include a blood infusate, but may include medications, drugs, nutrients, or other therapeutic fluids.

Flow may be achieved by either gravity-pressure or positive-pressure. Gravity-pressure based flow control systems rely on the force of gravity for fluid flow. Such systems may include an "IV controller" which interfaces with the IV tube. An IV controller is a device that automatically controls the flow rate of fluid through the IV tube by use of a pinching device that pinches the tube more or less to control the flow of fluid therethrough. An IV controller may be responsive to a control signal generated by, for example, a flow sensor attached to the drip chamber. The flow sensor senses fluid drops falling in the drip chamber, and a flow rate calculated based on counting the number of drops per unit time. If the calculated flow rate is greater than a desired flow rate, the controller adjusts the pinching device to lower the flow rate by pinching the tube further. Advantages of gravity administration sets include their relative simplicity and low cost. The pinching device comprises a relatively simple mechanical device under electrical control. IV controllers, however, are limited to gravity pressure, dependent upon the "head height" or "head pressure" of the administration fluid, which can be under 1 psi.

In certain situations the amount of pressure provided by a gravity-pressure based flow control device may be insufficient. In other situations, greater accuracy and precision of flow rates are required. In these situations a positive-pressure based flow control device is necessary.

Figure 2:
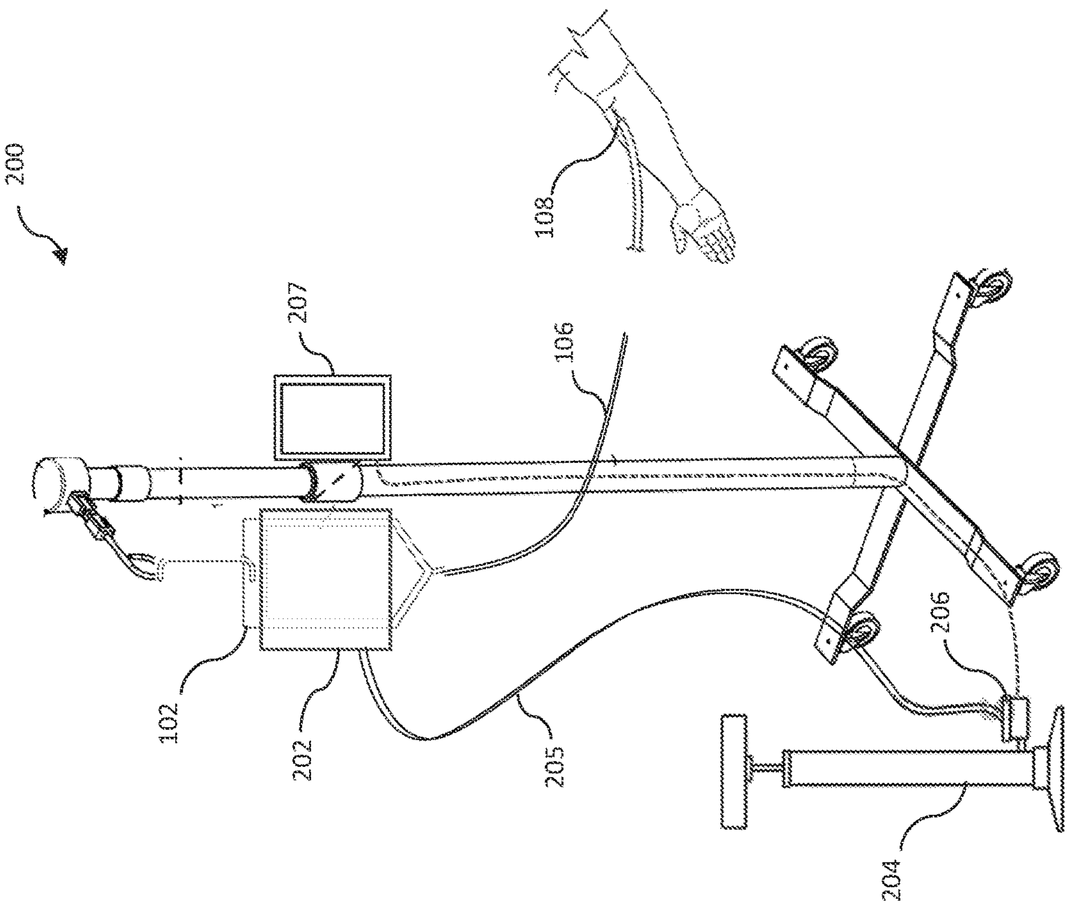
FIG. 2 depicts an example intravenous fluid delivery system coupled to a patient, according to various implementations of the subject technology.

FIG. 2 depicts an example intravenous fluid delivery system coupled to a patient, according to various implementations of the subject technology. The example delivery system 200 includes a fluid container 102 containing an intravenous (IV) fluid is held on an intravenous pole 104. According to various implementations, the fluid source is a malleable fluid container such as an IV bag or blood product bag. An infusion line 106 is connected to the malleable fluid container 102 for delivery of the fluid to the patient. The infusion line 106 may be a conventional IV infusion-type tube typically used in a hospital or medical environment, and is made of any type of flexible tubing appropriate for use to infuse therapeutic fluids into a patient, such as polyvinylchloride (PVC). A cannula 108 is mounted at the distal end of the flexible IV tubing for insertion into a patient's blood vessel or other body location to deliver the fluid to the patient.

With further reference to FIG. 2, the intravenous delivery system 200 includes a fluid container pressure sleeve 202 configured to wrap around, connect and form to the malleable fluid container. When the fluid container pressure sleeve 202 is inflated with a gas, the fluid container pressure sleeve 202 applies an inward directional pressure to the malleable fluid container from an exterior of the malleable fluid container. According to various implementations, the gas is air, but the gas used in the subject technology may also be an inert gas such as helium, argon, neon, xenon, or a combination of gases.

Figure 3B:
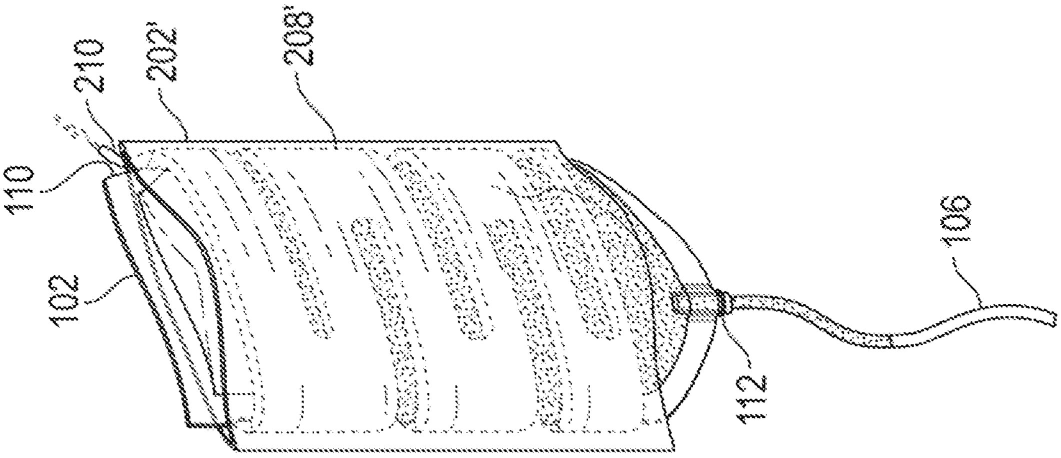
FIGS. 3A and 3B depict example fluid container pressure sleeves according to various implementations of the subject technology.
Figure 3A:
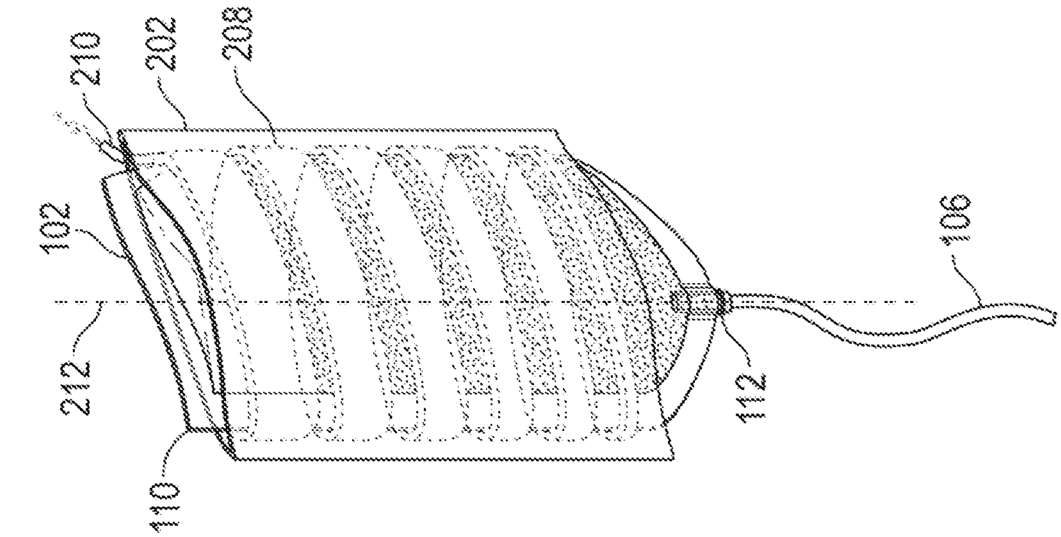

The fluid container pressure sleeve 202, explained further with reference to FIGS. 3A and 3B, may be a wrap that can be folded around the fluid container 102 and secured with Velcro attachment (e.g., integrated into sleeve 202), similar to a blood pressure cuff. The fluid container pressure sleeve 202 is, however, configured to conform to a shape of the malleable fluid container 202, both when the container is full of fluid and empty. In this regard, the fluid container pressure sleeve 202 may include attachments to maintain fixation to the fluid container while the container is hanging as depicted in FIG. 2, or when the container is otherwise moved. In some implementations, the fluid container pressure sleeve 202 may maintain a substantially flat shape so that, when its pressure chamber is inflated, it does not become rounded but, rather, maintains is form with respect to the relatively flat fluid container that it encompasses. As the fluid is expelled from the container, the fixation of the sleeve to the container maintain a constant flow. The sleeve may be made of a malleable and/or supple material to prevent damage (e.g., puncture or tearing) to the fluid container.

Intravenous delivery system 200 is further connected to a pump 204, which provides the gas to the fluid container pressure sleeve 202 via a gas line 205, and a pressure measuring device 206. According to various implementations, the measuring device 206 is configured to measure a pressure associated with the malleable fluid container by the fluid container pressure sleeve 202. According to some implementations, the pressure measured by the pressure measuring device 206 is indicative of a compression force applied to the malleable fluid container by the fluid container pressure sleeve 202. According to some implementations, the pressure measuring device 206 is configured to measure a fluid pressure of the fluid within the malleable fluid container. For example, the pressure may be measured by a force sensor (not shown) coupled to an exterior of the infusion line 106.

According to various implementations, the fluid container pressure sleeve 202 includes one or more internal gas chambers (see FIGS. 3A and 3B). Activating the pump comprises causes a gas to flow to within the gas chamber(s) via a connector and inflate the pressure sleeve 202, thereby compressing the fluid container and causing the fluid within the container to flow into and through the infusion line. According to various implementations, the chamber(s) within the pressure sleeve is configures such that the pressure sleeve bulges inward, compressing the fluid container, when being inflated.

In some implementations, the pressure measuring device comprises a pressure gauge. The pressure gauge may be a mechanical gauge with a dial face, or mercury column. In some implementations, the gauge may include pressure circuitry associated with pump 204 and/or gas line 205, and may, for example, include and/or be integrated with a user interface displayed on an electronic display device 207. For example, the pressure measuring device may include a sensor attached to the fluid container 102, infusion line 106, or fluid container pressure sleeve 202, which transmits a pressure signal which may then be interpreted by a computing device. The computing device may include or be operably connected to the electronic display device, and display a pressure value on an operably connected display device. In some implementations, the computing device and display device are the same device 207.

In some implementations, the pump is a hand pump. In some implementations, the pump is a foot controlled pump. In some implementations, the intravenous delivery system 200 includes a pump controller. The pump controller may include an electrical compressor configured to provide a metered amount of the gas to the fluid container pressure sleeve 202 based on a signal from the pump controller.

FIGS. 3A and 3B depict example fluid container pressure sleeves 202, 202' according to various implementations of the subject technology. According to various implementations, the disclosed fluid container pressure sleeve include an internal gas chamber 208 in a shape of a coil such that a helical axis of the coil traverses an axis of the malleable fluid container 102 when the fluid container pressure sleeve is wrapped around the malleable fluid container. In the example implementation of FIG. 3A, the internal coiled gas chamber 208 is integrated within and continuous around the sleeve 202. A connection point 210 is connected to the gas line 205 providing a gas from a gas source, such as the disclosed pump(s) 204. In the example implementation of FIG. 3B, the sleeve has two sides, and the internal coiled gas chamber includes two coiled circuits, with a coiled circuit integrated within each side of the sleeve. As depicted, the chambers may come together along the edges of the sleeve 202 so that they uniformly constrict the fluid container 102 therein. The circuits may each be connected to the same connection point 210, or may be joined by an internal coupling so that one of the chambers may be receive the gas from the connection point and the gas may be provided by the chamber to the other chamber.

With reference to both FIGS. 3A and 3B, a first end of the internal coiled gas chamber 208 is configured to, when the fluid container pressure sleeve 202 is wrapped around the malleable fluid container 102, terminate at a first end 110 of the malleable fluid container opposite a second end 112 of the malleable fluid container to which the infusion tubing is connected, and extend along the axis of the malleable fluid container toward the second end 112 of the malleable fluid container. With brief reference to FIG. 2, the internal coiled gas chamber 208 may terminate at the top 110 of the fluid container and extend down toward the bottom 112 of the container. According to various implementations, the sleeve 202 and internal gas chamber 208 is configured to bulge inward toward the fluid container 102 when inflated.

As depicted in FIGS. 3A and 3B, the internal coiled gas chamber 208 may incrementally increase in diameter toward the first end of the internal coiled gas chamber 208 (e.g., near the top 110 of the fluid container), from an end of the internal coiled gas chamber 208 opposite the first end of the internal coiled gas chamber. When the internal coiled gas chamber 208 is inflated, the internal coiled gas chamber may apply a greater pressure to an area near or at the first end 110 of the malleable fluid container (e.g., the top of the container when the container is hanging as in FIG. 2) than to an area closer to or at the second end of the malleable fluid container to which the infusion tubing 106 is connected. Thus, a flow of the fluid within the malleable fluid container 102 is caused to move in a direction 212 toward and through the connected infusion tubing 106.

The larger diameter portions of the internal coiled gas chamber 208 will bulge inward toward the fluid container 102, creating pressure on the fluid container 102. Because the coil 208 incrementally increases in diameter towards the top of the infusate bag, the bulging of the inflated coil chamber creates the greatest amount of pressure at the top of the bag (or first end 110), directing the flow of infusate downwards towards the patient direction optimizing the efficiency of the system.

Figure 4:
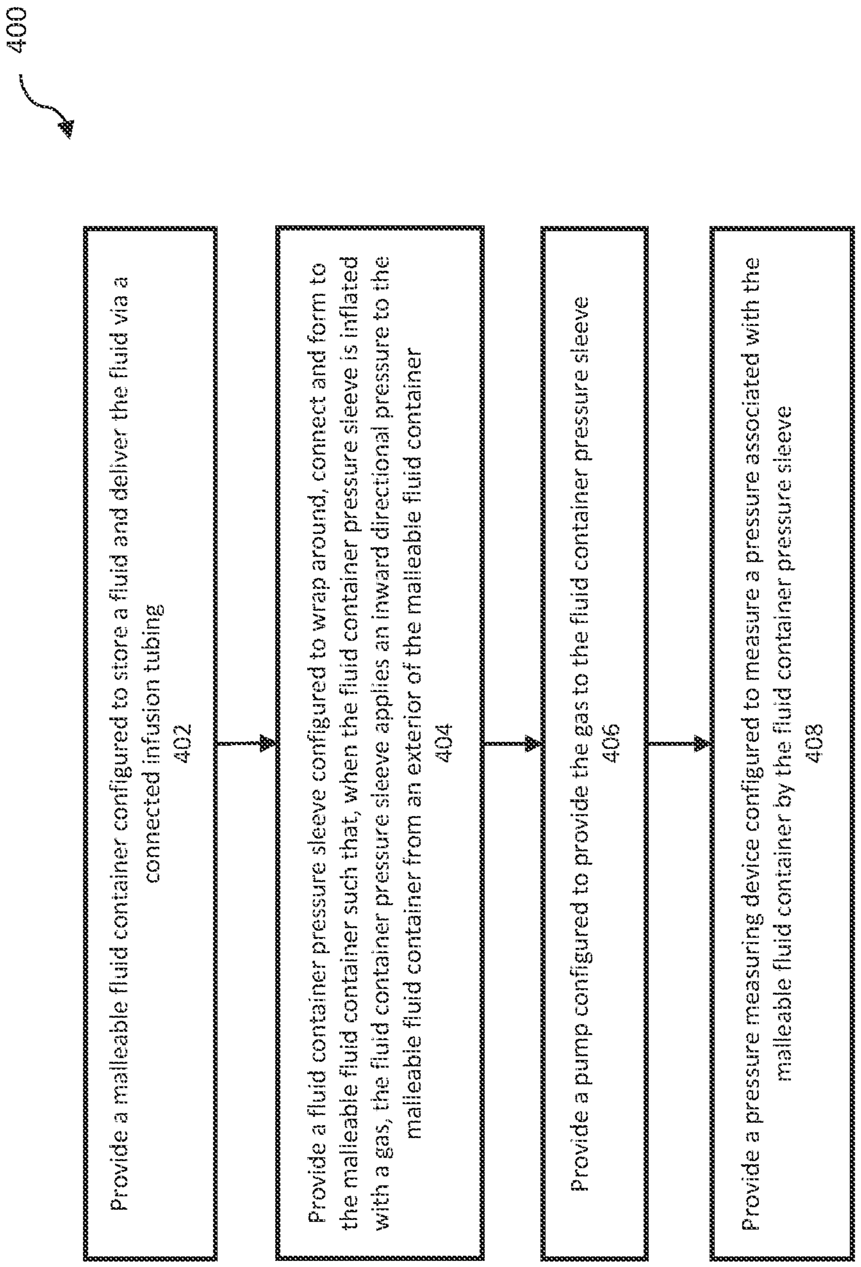
FIG. 4 depicts an example process for an intravenous delivery of an infusate from a fluid container, according to various implementations of the subject technology.

FIG. 4 depicts an example process for an intravenous delivery of an infusate from a fluid container, according to various implementations of the subject technology. For explanatory purposes, the various blocks of example process 400 are described herein with reference to FIGS. 1-3, and the components and/or processes described herein. In some implementations, one or more of the blocks may be implemented apart from other blocks, and by one or more different devices. Further for explanatory purposes, the blocks of example process 400 are described as occurring in serial, or linearly. However, multiple blocks of example process 400 may occur in parallel. In addition, the blocks of example process 400 need not be performed in the order shown and/or one or more of the blocks of example process 400 need not be performed.

In the depicted example, a malleable fluid container configured to store a fluid and deliver the fluid via a connected infusion tubing is provided (402). As described previously, the container may include an IV or blood product bag. A fluid container pressure sleeve 202 is also provided (404). The pressure sleeve is configured to wrap around, connect and form to the malleable fluid container such that, when the fluid container pressure sleeve 202 is inflated with a gas, the fluid container pressure sleeve 202 applies an inward directional pressure to the malleable fluid container from an exterior of the malleable fluid container.

According to various implementations, the fluid container pressure sleeve 202 includes an internal coiled gas chamber in a shape of a coil such that a helical axis of the coil traverses an axis of the malleable fluid container when the fluid container pressure sleeve 202 is wrapped around the malleable fluid container. A first end of the internal coiled gas chamber may be configured to, when the fluid container pressure sleeve 202 is wrapped around the malleable fluid container, terminate at a first end of the malleable fluid container opposite a second end of the malleable fluid container to which the infusion tubing is connected, and extend along the axis of the malleable fluid container toward the second end of the malleable fluid container.

In some implementations, the internal coiled gas chamber incrementally increases in diameter toward the first end of the internal coiled gas chamber from a second end of the internal coiled gas chamber opposite the first end of the internal coiled gas chamber, such that when the internal coiled gas chamber is inflated the internal coiled gas chamber applies a greater pressure to the first end of the malleable fluid container than the second end of the malleable fluid container to which the infusion tubing is connected, so as to direct a flow of the fluid within the malleable fluid container toward and through the connected infusion tubing.

A pump configured to provide the gas to the fluid container pressure sleeve 202 is provided (406). As described previously, the pump may be a hand pump or a foot pump. The pump may be a positive-displacement air pump. The pump may be a floor pump, a compact or mini pump and/or a piston pump. In some implementations, the pump may be an electric pump that, for example, includes a compressor. A pump controller may be provided that is configured to provide a metered amount of the gas to the fluid container pressure sleeve 202 based on a signal from the pump controller.

A pressure measuring device configured to measure a pressure associated with the malleable fluid container or the fluid container pressure sleeve 202 is provided (408). The pressure measuring device may be operably connected to the fluid container pressure sleeve 202 and configured to measure a pressure indicative of a compression force applied to the malleable fluid container by the fluid container pressure sleeve 202. The pressure measuring device may be configured to measure a fluid pressure of the fluid within the malleable fluid container, or a pressure applied to an exterior of the fluid container by the pressure sleeve 202.

Figure 5:
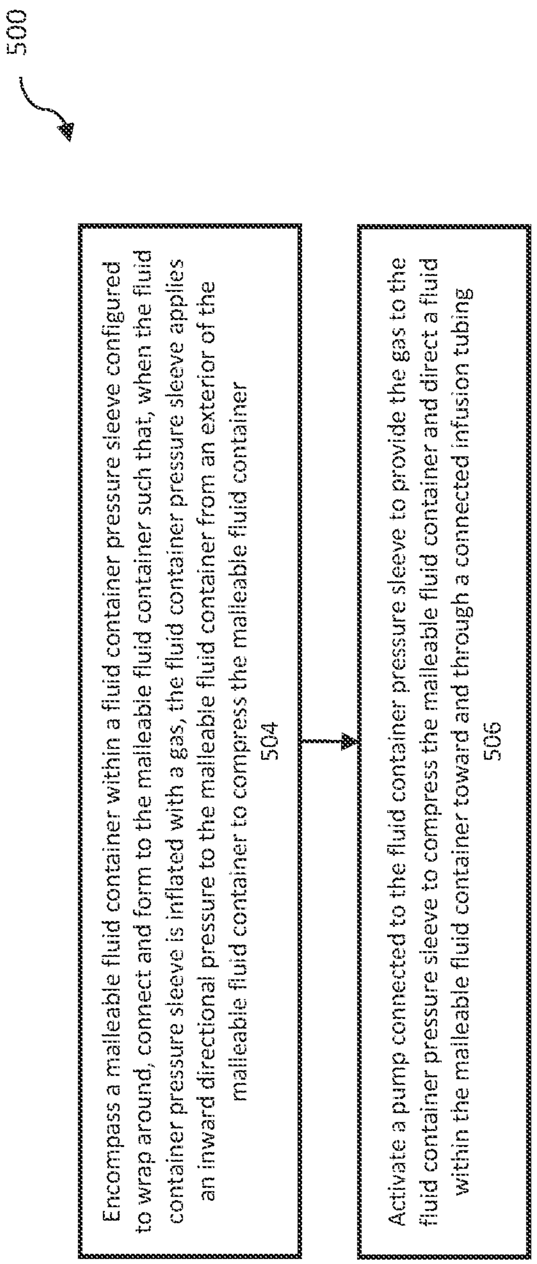
FIG. 5 depicts an example process for performing an intravenous delivery of an infusate from a fluid container, according to various implementations of the subject technology.

FIG. 5 depicts an example process for performing an intravenous delivery of an infusate from a fluid container, according to various implementations of the subject technology. For explanatory purposes, the various blocks of example process 400 are described herein with reference to FIGS. 1-4, and the components and/or processes described herein. In some implementations, one or more of the blocks may be implemented apart from other blocks, and by one or more different devices. Further for explanatory purposes, the blocks of example process 500 are described as occurring in serial, or linearly. However, multiple blocks of example process 500 may occur in parallel. In addition, the blocks of example process 500 need not be performed in the order shown and/or one or more of the blocks of example process 500 need not be performed.

The example process begins by encompassing a malleable fluid container within a fluid container pressure sleeve 202 configured to wrap around, connect and form to the malleable fluid container such that, when the fluid container pressure sleeve 202 is inflated with a gas, the fluid container pressure sleeve 202 applies an inward directional pressure to the malleable fluid container from an exterior of the malleable fluid container to compress the malleable fluid container (504).

A next step involves activating a pump connected to the fluid container pressure sleeve 202 to provide the gas to the fluid container pressure sleeve 202 to compress the malleable fluid container and direct a fluid within the malleable fluid container toward and through a connected infusion tubing (506). Activating the pump comprises causes an gas chamber within the pressure sleeve to fill with the gas and inflate, thereby compressing the fluid container and causing the fluid within the container to flow into and through the infusion line.

As described previously, the fluid container pressure sleeve 202 may include an internal coiled gas chamber in a shape of a coil such that a helical axis of the coil traverses an axis of the malleable fluid container when the fluid container pressure sleeve 202 is wrapped around the malleable fluid container. A first end of the internal coiled gas chamber is configured to, when the fluid container pressure sleeve 202 is wrapped around the malleable fluid container, terminate at a first end of the malleable fluid container (e.g., at the top of the container) opposite a second end of the malleable fluid container to which the infusion tubing is connected, and extend along the axis of the malleable fluid container toward the second end of the malleable fluid container. In this regard, the internal coiled gas chamber may be configured to incrementally increase in diameter toward the first end of the internal coiled gas chamber from a second end of the internal coiled gas chamber opposite the first end of the coiled gas chamber.

Activating the pump comprises causes the internal coiled gas chamber to apply a greater pressure to the first end of the malleable fluid container than the second end of the malleable fluid container to which the infusion tubing is connected, and to direct a flow of the fluid within the malleable fluid container toward and through the connected infusion tubing.

The use of a hand or foot operated pump can significantly reduce the fatigue experienced by the clinician as the exertion is not provided by the hand muscles but by the action of a hand or foot pushing a handle/peddle on the pump. These motions and ways of producing air pressure makes the device easy to use. Because this design does not require the use of power and is reusable, the cost of purchasing and operating this device may be low enough to be considered disposable. Additionally, in the case of the foot operated version, a clinician's hands would be freed to attend to the patient and the patients medical needs.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Illustration of Subject Technology as Clauses:

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A infusion system for intravenous delivery of a fluid from a fluid container, comprising: a malleable fluid container configured to store a fluid and deliver the fluid via a connected infusion tubing; a fluid container pressure sleeve configured to wrap around, connect and form to the malleable fluid container such that, when the fluid container pressure sleeve is inflated with a gas, the fluid container pressure sleeve applies an inward directional pressure to the malleable fluid container from an exterior of the malleable fluid container; a pump configured to provide the gas to the fluid container pressure sleeve; and a pressure measuring device configured to measure a pressure associated with the malleable fluid container by the fluid container pressure sleeve.

Clause 2. The infusion system of Clause 1, wherein the fluid container pressure sleeve comprises: an internal coiled gas chamber in a shape of a coil such that a helical axis of the coil traverses an axis of the malleable fluid container when the fluid container pressure sleeve is wrapped around the malleable fluid container.

Clause 3. The infusion system of Clause 2, wherein a first end of the internal coiled gas chamber is configured to, when the fluid container pressure sleeve is wrapped around the malleable fluid container, terminate at a first end of the malleable fluid container opposite a second end of the malleable fluid container to which the infusion tubing is connected, and extend along the axis of the malleable fluid container toward the second end of the malleable fluid container.

Clause 4. The infusion system of Clause 3, wherein the internal coiled gas chamber incrementally increases in diameter toward the first end of the internal coiled gas chamber from a second end of the internal coiled gas chamber opposite the first end of the internal coiled gas chamber, such that when the internal coiled gas chamber is inflated the internal coiled gas chamber applies a greater pressure to the first end of the malleable fluid container than the second end of the malleable fluid container to which the infusion tubing is connected, so as to direct a flow of the fluid within the malleable fluid container toward and through the connected infusion tubing.

Clause 5. The infusion system of any one of Clauses 1 to 4, wherein the pressure measuring device is configured to measure a fluid pressure of the fluid within the malleable fluid container.

Clause 6. The infusion system any one of Clauses 1 to 4, wherein the pressure measured by the pressure measuring device is indicative of a compression force applied to the malleable fluid container by the fluid container pressure sleeve.

Clause 7. The infusion system of any one of Clauses 1 to 6, wherein the pump is a hand pump.

Clause 8. The infusion system of any one of Clauses 1 to 6, wherein the pump is a foot controlled pump.

Clause 9. The infusion system of any one of Clauses 1 to 8, wherein the pressure measuring device comprises a pressure gauge.

Clause 10. The infusion system of any one of Clauses 1 to 9, further comprising: a pump controller, wherein the pump comprises an electrical compressor configured to provide a metered amount of the gas to the fluid container pressure sleeve based on a signal from the pump controller.

Clause 11. A method for intravenous delivery of a fluid from a fluid container, comprising: encompassing a malleable fluid container within a fluid container pressure sleeve configured to wrap around, connect and form to the malleable fluid container such that, when the fluid container pressure sleeve is inflated with a gas, the fluid container pressure sleeve applies an inward directional pressure to the malleable fluid container from an exterior of the malleable fluid container to compress the malleable fluid container; and activating a pump connected to the fluid container pressure sleeve to provide the gas to the fluid container pressure sleeve to compress the malleable fluid container and direct a fluid within the malleable fluid container toward and through a connected infusion tubing.

Clause 12. The method of Clause 11, wherein the fluid container pressure sleeve comprises: an internal coiled gas chamber in a shape of a coil such that a helical axis of the coil traverses an axis of the malleable fluid container when the fluid container pressure sleeve is wrapped around the malleable fluid container, wherein a first end of the internal coiled gas chamber is configured to, when the fluid container pressure sleeve is wrapped around the malleable fluid container, terminate at a first end of the malleable fluid container opposite a second end of the malleable fluid container to which the infusion tubing is connected, and extend along the axis of the malleable fluid container toward the second end of the malleable fluid container, wherein activating the pump comprises causing the internal coiled gas chamber to fill with the gas and inflate.

Clause 13. The method of Clause 12, wherein the internal coiled gas chamber incrementally increases in diameter toward the first end of the internal coiled gas chamber from a second end of the internal coiled gas chamber opposite the first end of the coiled gas chamber, wherein activating the pump comprises causing the internal coiled gas chamber to apply a greater pressure to the first end of the malleable fluid container than the second end of the malleable fluid container to which the infusion tubing is connected, and direct a flow of the fluid within the malleable fluid container toward and through the connected infusion tubing.

Clause 14. A method for intravenous delivery of a fluid from a fluid container, comprising: providing a malleable fluid container configured to store a fluid and deliver the fluid via a connected infusion tubing; providing a fluid container pressure sleeve configured to wrap around, connect and form to the malleable fluid container such that, when the fluid container pressure sleeve is inflated with a gas, the fluid container pressure sleeve applies an inward directional pressure to the malleable fluid container from an exterior of the malleable fluid container; providing a pump configured to provide the gas to the fluid container pressure sleeve; and providing a pressure measuring device configured to measure a pressure associated with the malleable fluid container by the fluid container pressure sleeve.

Clause 15. The method of Clause 14, wherein the fluid container pressure sleeve comprises: an internal coiled gas chamber in a shape of a coil such that a helical axis of the coil traverses an axis of the malleable fluid container when the fluid container pressure sleeve is wrapped around the malleable fluid container, wherein a first end of the internal coiled gas chamber is configured to, when the fluid container pressure sleeve is wrapped around the malleable fluid container, terminate at a first end of the malleable fluid container opposite a second end of the malleable fluid container to which the infusion tubing is connected, and extend along the axis of the malleable fluid container toward the second end of the malleable fluid container.

Clause 16. The method of Clause 15, wherein the internal coiled gas chamber incrementally increases in diameter toward the first end of the internal coiled gas chamber from a second end of the internal coiled gas chamber opposite the first end of the internal coiled gas chamber, such that when the internal coiled gas chamber is inflated the internal coiled gas chamber applies a greater pressure to the first end of the malleable fluid container than the second end of the malleable fluid container to which the infusion tubing is connected, so as to direct a flow of the fluid within the malleable fluid container toward and through the connected infusion tubing.

Clause 17. The method of any one of Clauses 14 to 16, further comprising: providing a pressure measuring device operably connected to the fluid container pressure sleeve and configured to measure a pressure indicative of a compression force applied to the malleable fluid container by the fluid container pressure sleeve.

Clause 18. The method of any one of Clauses 14 to 16, further comprising: providing a pressure measuring device operably connected to the malleable fluid container and configured to measure a fluid pressure of the fluid within the malleable fluid container.

Clause 19. The method of any one of Clauses 14 to 18, wherein the pump is a hand pump or a foot controlled pump.

Clause 20. The method of any one of Clauses 14 to 19, further comprising: providing a pump controller comprising an electrical compressor configured to provide a metered amount of the gas to the fluid container pressure sleeve based on a signal from the pump controller.

Further Consideration:

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The predicate words "configured to", "operable to", and "programmed to" do not imply any particular tangible or intangible modification of a subject, but, rather, are intended to be used interchangeably. For example, a processor configured to monitor and control an operation or a component, may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as an "implementation" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, C, C++, web services, or rich site summary (RSS). In some implementations, a UI may be included in a stand-alone client (for example, thick client, fat client) configured to communicate (e.g., send or receive data) in accordance with one or more of the aspects described. The communication may be to or from a medical device or server in communication therewith.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In some implementations, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

What is claimed is:

1. An infusion system for intravenous delivery of a fluid from a malleable fluid container, comprising:

the malleable fluid container configured to store a fluid and deliver the fluid via a connected infusion tubing;

a fluid container pressure sleeve configured to wrap around, connect and form to the malleable fluid container such that, when the fluid container pressure sleeve is inflated with a gas, the fluid container pressure sleeve applies an inward directional pressure to the malleable fluid container from an exterior of the malleable fluid container, the fluid container pressure sleeve comprises an internal coiled gas chamber in a shape of a coil such that:

a helical axis of the coil traverses a longitudinal axis of the malleable fluid container when the fluid container pressure sleeve is wrapped around the malleable fluid container and a diameter of an internal coil of the internal coiled gas chamber incrementally increases toward a first end of the internal coiled gas chamber from a second end of the internal coiled gas chamber opposite the first end of the internal coiled gas chamber, such that when the internal coiled gas chamber is inflated the internal coiled gas chamber applies a greater pressure to a first end of the malleable fluid container than the second end of the malleable fluid container to which the infusion tubing is connected;

a pump configured to provide the gas to the fluid container pressure sleeve; and a pressure measuring device configured to measure a pressure associated with the malleable fluid container by the fluid container pressure sleeve.

2. The infusion system of claim 1, wherein the first end of the internal coiled gas chamber is configured to, when the fluid container pressure sleeve is wrapped around the malleable fluid container, terminate at the first end of the malleable fluid container opposite the second end of the malleable fluid container to which the infusion tubing is connected, and extend along the longitudinal axis of the malleable fluid container toward the second end of the malleable fluid container.

3. The infusion system of claim 1, wherein when the internal coiled gas chamber is inflated the internal coiled gas chamber applies the greater pressure to the first end of the malleable fluid container so as to direct a flow of the fluid within the malleable fluid container toward and through the connected infusion tubing.

4. The infusion system of claim 1, wherein the pressure measuring device is configured to measure a fluid pressure of the fluid within the malleable fluid container.

5. The infusion system of claim 1, wherein the pressure measured by the pressure measuring device is indicative of a compression force applied to the malleable fluid container by the fluid container pressure sleeve.

6. The infusion system of claim 1, wherein the pump is a hand pump.

7. The infusion system of claim 1, wherein the pump is a foot controlled pump.

8. The infusion system of claim 1, wherein the pressure measuring device comprises a pressure gauge.

9. The infusion system of claim 1, further comprising:

a pump controller, wherein the pump comprises an electrical compressor configured to provide a metered amount of the gas to the fluid container pressure sleeve based on a signal from the pump controller.

10. A method for intravenous delivery of a fluid from a malleable fluid container, comprising:

encompassing the malleable fluid container within a fluid container pressure sleeve configured to wrap around, connect and form to the malleable fluid container such that, when the fluid container pressure sleeve is inflated with a gas, the fluid container pressure sleeve applies an inward directional pressure to the malleable fluid container from an exterior of the malleable fluid container to compress the malleable fluid container and the fluid container pressure sleeve comprises an internal coiled gas chamber in a shape of a coil such that:

a helical axis of the coil traverses a longitudinal axis of the malleable fluid container when the fluid container pressure sleeve is wrapped around the malleable fluid container and a diameter of an internal coil of the internal coiled gas chamber incrementally increases toward a first end of the internal coiled gas chamber from a second end of the internal coiled gas chamber opposite the first end of the internal coiled gas chamber, such that when the internal coiled gas chamber is inflated the internal coiled gas chamber applies a greater pressure to a first end of the malleable fluid container than the second end of the malleable fluid container to which an infusion tubing is connected; and activating a pump connected to the fluid container pressure sleeve to provide the gas to the fluid container pressure sleeve to compress the malleable fluid container and direct a fluid within the malleable fluid container toward and through the connected infusion tubing.

11. The method of claim 10, wherein the first end of the internal coiled gas chamber is configured to, when the fluid container pressure sleeve is wrapped around the malleable fluid container, terminate at the first end of the malleable fluid container opposite the second end of the malleable fluid container to which the infusion tubing is connected, and extend along the longitudinal axis of the malleable fluid container toward the second end of the malleable fluid container; and activating the pump comprises causing the internal coiled gas chamber to fill with the gas and inflate.

12. The method of claim 11, wherein activating the pump comprises causing the internal coiled gas chamber to apply the greater pressure to the first end of the malleable fluid container to direct a flow of the fluid within the malleable fluid container toward and through the connected infusion tubing.

13. A method for intravenous delivery of a fluid from a malleable fluid container, comprising:

providing the malleable fluid container configured to store a fluid and deliver the fluid via a connected infusion tubing;

providing a fluid container pressure sleeve configured to wrap around, connect and form to the malleable fluid container such that, when the fluid container pressure sleeve is inflated with a gas, the fluid container pressure sleeve applies an inward directional pressure to the malleable fluid container from an exterior of the malleable fluid container and the fluid container pressure sleeve comprises an internal coiled gas chamber in a shape of a coil such that:

a helical axis of the coil traverses a longitudinal axis of the malleable fluid container when the fluid container pressure sleeve is wrapped around the malleable fluid container and a diameter of an internal coil of the internal coiled gas chamber incrementally increases toward a first end of the internal coiled gas chamber from a second end of the internal coiled gas chamber opposite the first end of the internal coiled gas chamber, such that when the internal coiled gas chamber is inflated the internal coiled gas chamber applies a greater pressure to a first end of the malleable fluid container than the second end of the malleable fluid container to which the infusion tubing is connected;

providing a pump configured to provide the gas to the fluid container pressure sleeve; and providing a pressure measuring device configured to measure a pressure associated with the malleable fluid container by the fluid container pressure sleeve.

14. The method of claim 13, wherein the first end of the internal coiled gas chamber is configured to, when the fluid container pressure sleeve is wrapped around the malleable fluid container, terminate at the first end of the malleable fluid container opposite the second end of the malleable fluid container to which the infusion tubing is connected, and extend along the longitudinal axis of the malleable fluid container toward the second end of the malleable fluid container.

15. The method of claim 14, wherein when the internal coiled gas chamber is inflated the internal coiled gas chamber applies the greater pressure to the first end of the malleable fluid container so as to direct a flow of the fluid within the malleable fluid container toward and through the connected infusion tubing.

16. The method of claim 13, further comprising:

providing a pressure measuring device operably connected to the fluid container pressure sleeve and configured to measure a pressure indicative of a compression force applied to the malleable fluid container by the fluid container pressure sleeve.

17. The method of claim 13, further comprising:

providing a pressure measuring device operably connected to the malleable fluid container and configured to measure a fluid pressure of the fluid within the malleable fluid container.

18. The method of claim 13, wherein the pump is a hand pump or a foot controlled pump.

19. The method of claim 13, further comprising:

providing a pump controller comprising an electrical compressor configured to provide a metered amount of the gas to the fluid container pressure sleeve based on a signal from the pump controller.

* * * * *